(12) United States Patent
Jin et al.

(10) Patent No.: US 7,271,005 B2
(45) Date of Patent: Sep. 18, 2007

(54) MODULATION OF BACTERIAL MEMBRANE PERMEABILITY

(75) Inventors: Shouguang Jin, Gainesville, FL (US); Unhwan Ha, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/425,241

(22) Filed: Apr. 29, 2003

(65) Prior Publication Data

US 2003/0232412 A1 Dec. 18, 2003

Related U.S. Application Data

(60) Provisional application No. 60/376,597, filed on Apr. 30, 2002.

(51) Int. Cl.
*C12N 15/74* (2006.01)
*C12N 15/00* (2006.01)
*C12N 1/20* (2006.01)

(52) U.S. Cl. ............... 435/476; 435/320.1; 435/252.3; 435/252.33

(58) Field of Classification Search ............... 435/471, 435/252.3, 252.34, 320.1
See application file for complete search history.

(56) References Cited

FOREIGN PATENT DOCUMENTS

WO WO89/09823 * 10/1989

OTHER PUBLICATIONS

Stover et al., "Complete genome sequence of *Pseudomonas aeruginosa* PAO1, and opportunistic pathogen", Nature, vol. 406: 959-964 (2000).*

Poole et al., "Expression of the Multidrug Resistance Operon mexA-mexB-oprM in *Pseudomonas aeruginosa*: mexR Encodes a Regulator of Operon Expression," Antimicrobial Agents and Chemotherapy 40:2021-2028, 1996.

Nicas et al., "*Pseudomonas aeruginosa* Outer Membrane Permeability: Isolation of a Porin Protein F-Deficient Mutant," J. Bacteriol. 153:281-285, 1983.

Sampson et al., "Identification and Characterization of a New Gene of *Escherichia coli* K-12 Involved in Outer Membrane Permeability," Genetics122:491-501, 1989.

Shawar et al., "Activities of Tobramycin and Six Other Antibiotics against *Pseudomonas aeruginosa* Isolates from Patients with Cystic Fibrosis," Antimicrobial Agents and Chemotherapy, 43: 2877-2880, 1999.

Burns et al., "Effects of Chronic Intermittent Administration of Inhaled Tobramycin on Respiratory Microbial Flora in Patients with Cystic Fibrosis," The Journal of Infectious Diseases, 179: 1190-1196, 1999.

"Pas domain-S-boxes in Archaa, Bacteria and sensors for oxygen and redox," Protein Sequence Motif, 22: 331-333, 1997.

Wang et al., "Regulation of Membrane Permeability by a Two-Component Regulatory System in *Pseudomonas aeruginosa*," Antimicrobial Agents and Chemotherapy, 47: 95-101, 2003.

(Continued)

*Primary Examiner*—Nancy Vogel
(74) *Attorney, Agent, or Firm*—Akerman Senterfitt; Nicholas Zachariades

(57) ABSTRACT

Nucleic acids and polypeptides involved in regulation of membrane permeability in bacteria are disclosed. Also disclosed are methods of increasing sensitivity to antibiotics in multi-drug resistant bacteria by increasing expression of PprA or PprB proteins in bacterial cells, and methods for identifying compounds that modulate PprA/PprB expression.

12 Claims, 1 Drawing Sheet

OTHER PUBLICATIONS

Ouchane, S. and Samuel Kaplan, "Topological Analysis of the Membrane-localized Redox-responsive Sensor Kinase PrrB from *Rhodobacter sphaeroides* 2.4.1," The Journal of Biological Chemistry, 274: 17290-17296, 1999.

Martinez et al., "Kinetic Properties of Enzyme Populations in Viv: Alkaline Phosphatase of the *Escherichia coli* Periplasm", Biochemistry, 31: 11500-11509, 1992.

* cited by examiner

MODULATION OF BACTERIAL MEMBRANE PERMEABILITY

CROSS-REFERENCE TO RELATED APPLICATIONS

The present application claims the priority of U.S. provisional patent application number 60/376,597 filed Apr. 30, 2002.

STATEMENT AS TO FEDERALLY FUNDED RESEARCH

This invention was made with United States government support under grant number AI39524 awarded by National Institutes of Health. The United States government may have certain rights in the invention.

FIELD OF THE INVENTION

The invention relates generally to the fields of bacteriology, infectious diseases and medicine. More particularly, the invention relates to methods and compositions for modulating bacterial membrane permeability and antibiotic sensitivity.

BACKGROUND

*Pseudomonas aeruginosa* is an opportunistic pathogen which poses a major threat to immunocompromised patients, burn victims, and cystic fibrosis (CF) patients. More than 90% of the mortality among CF patients is caused by lung infection with *P. aeruginosa*. Saiman et al., 1996, Clin Infect Dis. 23 (3): 532-7; Shawar et al., 1999, Antimicrob Agents Chemother. 43 (12): 2877-80. CF patients acquire *P. aeruginosa* infection from the environment at an early age. Repeated treatment with various antibiotics selects for multi-drug resistant strains. Alonso et al., 1999, Microbiology, 145 (Pt 10): 2857-62.

A number of mechanisms by which bacteria become resistant to antibiotics are known. Among these are enzymatic inactivation of the drug, alteration of drug target sites, development of bypass pathways around drug targets, and reduction in cell-wall membrane permeability. While most types of drug resistance are antibiotic-specific, membrane permeability reduction usually results in a multi-drug resistant phenotype. Reduced membrane permeability is common among clinical isolates of *P. aeruginosa*. Indeed, the vast majority of CF isolates exhibit reduced membrane permeability and a multi-drug resistant phenotype. Burns et al., 1999, J Infect Dis. 179 (5):1190-6; Shawar et al., supra. Although many of the molecular mechanisms underlying specific antibiotic resistance are well known, they remain poorly understood in multi-drug resistance.

SUMMARY

The invention relates to the discovery of a two-component regulatory system that modulates bacterial membrane permeability and antibiotic sensitivity. The components include PprA encoded by the pprA gene and PprB encoded by the pprB gene. Overexpression of pprB reduced aminoglycoside-resistance in clinical isolates of *P. aeruginosa*. Elevated expression of PprA/PprB also increased the outer membrane permeability in *P. aeruginosa*.

Accordingly, the invention features a non-naturally occurring method including a step of modulating expression of PprA and/or PprB in a bacterium (e.g., a *Pseudomonas aeruginosa* bacterium). This step can be accomplished by introducing into the bacterium a nucleic acid encoding PprA and/or PprB (e.g., the polynucleotide of SEQ ID NO:1 or SEQ ID NO:2). Performing the above method can result in a change in membrane permeability in the bacterium and/or a change in antibiotic (e.g., aminoglycoside) sensitivity of the bacterium.

In another aspect, the invention features a bacterium into which has been introduced an agent that modulates in the bacterium expression of PprA and/or PprB. The agent can be a nucleic acid encoding PprA and/or PprB (e.g., the polynucleotide of SEQ ID NO:1 or SEQ ID NO:2). The invention further features a vector having a promoter operably linked to a nucleic acid encoding PprA and/or Ppr.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules.

By the terms "pprA gene," pprA polynucleotide," or "pprA nucleic acid" is meant a native PprA-encoding nucleic acid sequence, e.g., the native PprA DNA (SEQ ID NO:1); a nucleic acid having sequences from which PprA DNA can be transcribed; and/or allelic variants and homologs of the foregoing. Similar terms apply to designations for the pprb gene. The terms encompass double-stranded DNA, single-stranded DNA, and RNA.

As used herein, "protein" or "polypeptide" are used synonymously to mean any peptide-linked chain of amino acids, regardless of length or post-translational modification, e.g., glycosylation or phosphorylation. A "purified" polypeptide is one that has been substantially separated or isolated away from other polypeptides in a cell or organism in which the polypeptide naturally occurs (e.g., 30, 40, 50, 60, 70, 80, 90, 95, 96, 97, 98, 99, 100% free of contaminants).

By the terms "PprA," "PprA protein," or "PprA polypeptide" is meant an expression product of a pprA gene such as the native PprA protein shown herein as SEQ ID NO:3; a protein that shares at least 65% (but preferably 75, 80, 85, 90, 95, 96, 97, 98, or 99%) amino acid sequence identity with the protein of SEQ ID NO:3 and displays a functional activity of a native PprA; or a fragment of one of the foregoing that displays a functional activity of a native PprA. Similarly, by the terms "PprB," "PprB protein," or "PprB polypeptide" is meant an expression product of a pprB gene such as the native PprB protein shown herein as SEQ ID NO:4; a protein that shares at least 65% (but preferably 75, 80, 85, 90 , 95, 96, 97 ,98, or 99%) amino acid sequence identity with the protein of SEQ ID NO:4 and displays a functional activity of a native PprA; or a fragment of one of the foregoing that displays a functional activity of a native PprB. A "functional activity" of a protein is any activity associated with a physiological function of the protein. For example, functional activities of PprA or PprB may include control of membrane permeability or antibiotic-resistance in bacteria. Functional activities of PprA may include phosphorylation of PprB.

When referring to a nucleic acid molecule or polypeptide, the term "native" refers to a naturally-occurring (e.g., a "wild-type") nucleic acid or polypeptide. A "homolog" of a pprA gene is a gene sequence encoding a PprA polypeptide isolated from an organism other than P. aeruginosa. Similarly, a "homolog" of a native PprA polypeptide is an expression product of a PprA homolog. Similarly terminology applies to homologs of naturally occurring pprB nucleic acid and PprB polypeptides.

A "fragment" of a pprA nucleic acid is a portion of a pprA nucleic acid that is less than full-length and comprises at least a minimum length capable of hybridizing specifically with a native pprA nucleic acid under stringent hybridization conditions. The length of such a fragment is preferably at least 15 nucleotides, more preferably at least 20 nucleotides, and most preferably at least 30 nucleotides of a native PprA nucleic acid sequence. A "fragment" of a PprA polypeptide is a portion of a PprA polypeptide that is less than full-length (e.g., a polypeptide consisting of 5, 10, 15, 20, 30, 40, 50, 75, 100 or more amino acids of native PprA polypeptide), and preferably retains at least one functional activity of native PprA polypeptide. The term "fragment" is used likewise to refer to less than full-length portions of a pprb nucleic acid or PprB protein.

When referring to hybridization of one nucleic to another, "low stringency conditions" means in 10% formamide, 5×Denhart's solution, 6×SSPE, 0.2% SDS at 42° C., followed by washing in 1×SSPE, 0.2% SDS, at 50° C.; "moderate stringency conditions" means in 50% formamide, 5×Denhart's solution, 5×SSPE, 0.2% SDS at 42° C., followed by washing in 0.2×SSPE, 0.2% SDS, at 65° C.; and "high stringency conditions" means in 50% formamide, 5×Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. As another example, if 12 positions in a protein sequence 20 amino acids in length are identical to the corresponding positions in a second 20-amino acid sequence, then the two sequences have 60% sequence identity. Preferably, the length of the compared nucleic acid sequences is at least 60 nucleotides, more preferably at least 75 nucleotides, and most preferably 100 nucleotides; and the length of compared polypeptide sequences is at least 15, 25, and 50 amino acids. Sequence identity is typically measured using sequence analysis software (e.g., Sequence Analysis Software Package of the Genetics Computer Group, University of Wisconsin Biotechnology Center, 1710 University Avenue, Madison, Wis. 53705).

As used herein, the term "vector" refers to a nucleic acid molecule capable of transporting another nucleic acid to which it has been linked.

A first nucleic acid sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ moles/liter for that second molecule.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

DETAILED DESCRIPTION

Figure 1:
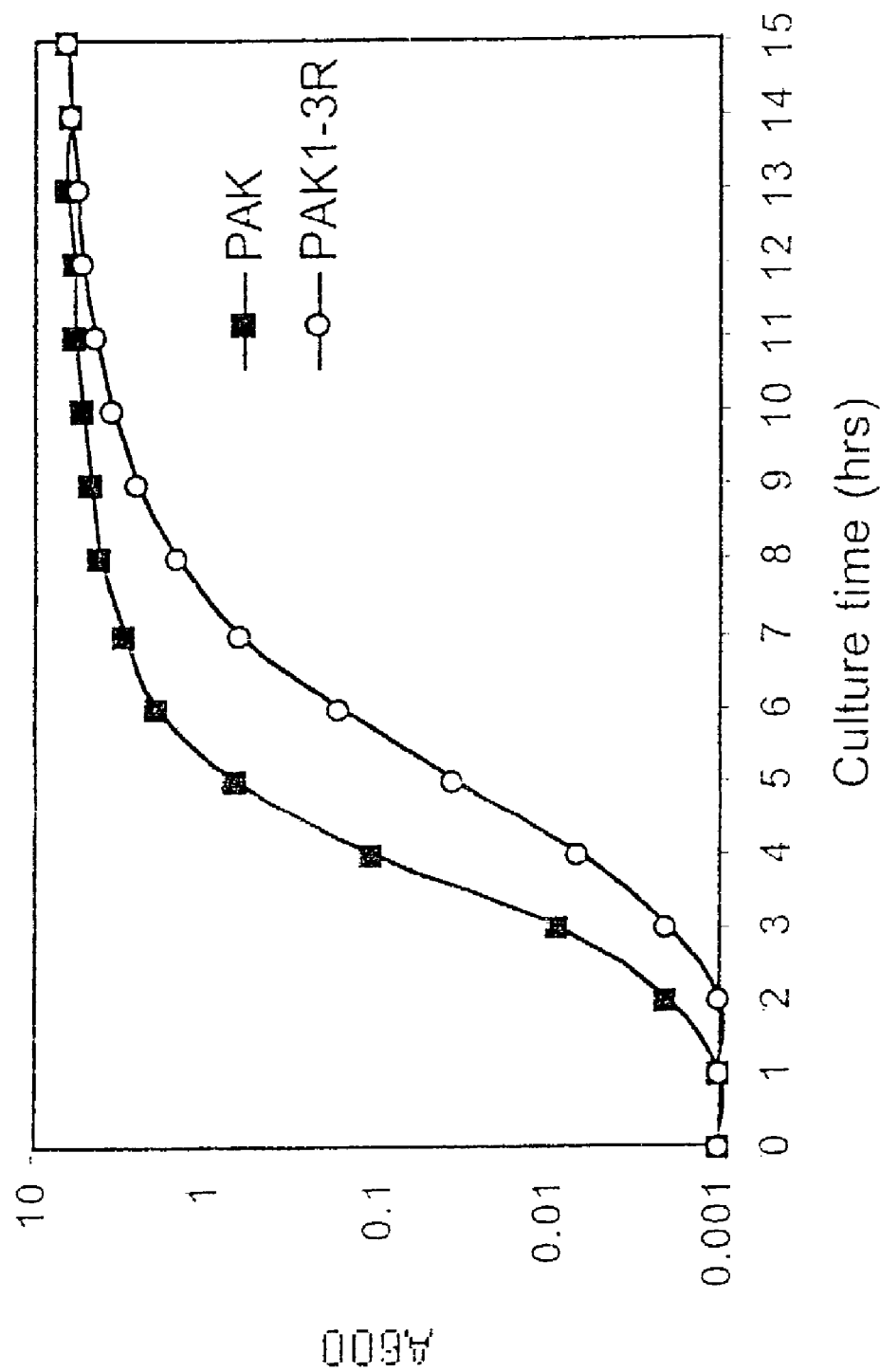
FIG. 1 is a graph showing a comparison of outer membrane permeability among different bacterial strains using a whole cell alkaline phosphatase assay.

The invention encompasses compositions and methods relating to regulation of membrane permeability and antibiotic-resistance in bacteria. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. PCR-primer pairs can be derived from known sequences by known techniques such as using computer programs intended for that purpose (e.g., Primer, Version 0.5, ©1991, Whitehead Institute for Biomedical Research, Cambridge, Mass.). The Reverse Transcriptase Polymerase Chain Reaction (RT-PCR) method used to identify and amplify certain polynuleotide sequences within the invention was performed as described in Elek et al., In Vivo, 14:172-182, 2000). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Nucleic Acids Encoding PprA or PprB

The present invention utilizes pprA or pprB genes, which have now been cloned and sequenced. A preferred nucleic acid molecule for use in the invention is the native pprA polynucleotide shown herein as SEQ ID NO: 1. Another preferred nucleic acid molecule that can be used in the various aspects of the invention is the native pprB polynucleotide shown herein as SEQ ID NO: 2. Other nucleic acids that can be used in the invention include a purified nucleic acid (polynucleotide) that encodes a polypeptide having the amino acid sequence of SEQ ID NO:3 and a purified nucleic acid having the amino acid sequence of SEQ ID NO:4. As the native pprA or pprB genes were originally cloned from the laboratory strain of Pseudomonas aeruginosa known as PAK, nucleic acid molecules encoding a polypeptide of the present invention can be obtained from a genomic library prepared from PAK by conventional cloning methods such as those described herein.

Nucleic acid molecules utilized in the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes the native PprA protein may be identical to the nucleotide sequence shown herein as SEQ ID NO: 1. It may also be a different coding sequence which, as a result of the redundancy or degeneracy of the genetic code, encodes the same polypeptide as the polynucleotide of SEQ ID NO: 1. Similarly, the coding sequence which encodes the native PprB protein may be identical to the nucleotide sequence shown herein as SEQ ID NO: 2. It may also be a different coding sequence which, as a result of the redundancy or degeneracy of the genetic code, encodes the same polypeptide as the polynucleotide of SEQ ID NO:2.

Other nucleic acid molecules within the invention are variants of the native pprA or pprB genes such as those that encode fragments, analogs and derivatives of a native PprA or PprB protein. Such variants may be, e.g., naturally occurring allelic variants of the native pprA or pprB genes, homologs of the native pprA or pprB genes, or non-naturally occurring variants of the native pprA or pprB genes. These variants have a nucleotide sequence that differs from the native pprA or pprB genes in one or more bases. For example, the nucleotide sequence of such variants can feature a deletion, addition, or substitution of one or more nucleotides of the native pprA or pprB genes. Nucleic acid insertions are preferably of about 1 to 10 contiguous nucleotides, and deletions are preferably of about 1 to 30 contiguous nucleotides.

In other applications, variant PprA or PprB proteins displaying substantial changes in structure can be generated by making nucleotide substitutions that cause less than conservative changes in the encoded polypeptides. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of the native pprA gene within the invention are nucleic acids isolated from Pseudomonas aeruginosa at have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native pprA gene, and encode polypeptides having structural similarity to native PprA protein. Homologs of the native pprA gene within the invention are nucleic acids isolated from other species that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native pprA gene, and encode polypeptides having structural similarity to native PprA protein. Similarly, naturally occurring allelic variants of the native pprB gene within the invention are nucleic acids isolated from Pseudomonas aeruginosa that have at least 75% (e.g., 76%, 77%, 78%, 79%, 80%, 81%, 82%, 83%, 84%, 85%, 86%, 88%, 89%, 90%, 91%, 92%, 93%, 94%, 95%, 96%, 97%, 98%, and 99%) sequence identity with the native pprB gene, and encode polypeptides having structural similarity to native PprB protein. Homologs of the native pprB gene within the invention are nucleic acids isolated from other species that have at least 75% (e.g., 76%, 77%, 78%, 79%, 80%, 81%, 82%,83%,84%, 85%, 86%, 87%, 88%, 89%, 90%, 91%, 92%, 93%, 94%, 95%, 96%, 97%, 98%, and 99%) sequence identity with the native pprB gene, and encode polypeptides having structural similarity to native PprB protein. Public and/or proprietary nucleic acid databases can be searched in an attempt to identify other nucleic acid molecules having a high percent (e.g., 70, 80, 90% or more) sequence identity to the native pprA or pprB genes.

Non-naturally occurring pprA gene variants are nucleic acids that do not occur in nature (e.g., are made by the hand of man), have at least 75% (e.g., 76%, 77%, 78%, 79%, 80%, 81%, 82%, 83%, 84%, 85%, 86%, 87%, 88%,89%, 90%, 91%, 92%, 93%, 94%, 95%, 96%, 97%, 98%, and 99%) sequence identity with the native pprA gene, and encode polypeptides having structural similarity to native PprA protein. Examples of non-naturally occurring pprA gene variants are those that encode a fragment of a PprA protein, those that hybridize to the native pprA gene or to a complement of the native pprA gene under stringent conditions, those that share at least 65% sequence identity with the native pprA gene or a complement of the native pprA gene, and those that encode a PprA fusion protein. Similarly, non-naturally occurring pprB gene variants are nucleic acids that do not occur in nature (e.g., are made by the hand of man), have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with the native pprB gene, and encode polypeptides having structural similarity to native PprB protein. Examples of non-naturally occurring pprB gene variants are those that encode a fragment of a PprB protein, those that hybridize to the native pprB gene or to a complement of the native pprB gene under stringent conditions, those that share at least 65% sequence identity with the native pprB gene or a complement of the native pprB gene, and those that encode an PprB fusion protein.

Nucleic acids encoding fragments of native PprA protein within the invention are those that encode, e.g., 2, 5, 10, 25, 30, 40, 50, 60, 70, 80, 90, 100, or more amino acid residues of the native PprA protein. Shorter oligonucleotides (e.g., those of 6, 7, 8, 9, 10, 11, 12, 13, 14, 15, 16, 17, 18, 19, 20, 30, 50, 100, base pairs in length) that encode or hybridize with nucleic acids that encode fragments of the native PprA protein can be used as probes, primers, or antisense molecules. Longer polynucleotides (e.g., those of 125, 150, 175, 200, 225, 250, 275, 300, or more base pairs) that encode or hybridize with nucleic acids that encode fragments of native PprA protein can also be used in various aspects of the invention. Nucleic acids encoding fragments of native PprA protein can be made by enzymatic digestion (e.g., using a restriction enzyme) or chemical degradation of the full length native pprA gene or variants thereof. Similarly, nucleic acids encoding fragments of native PprB protein of the invention can be used.

Nucleic acids that hybridize under stringent conditions to the nucleic acid of SEQ ID NO: 1 or the complement of SEQ ID NO: 1 can also be used in the invention. For example, such nucleic acids can be those that hybridize to SEQ ID NO: 1 or the complement of SEQ ID NO: 1 under low stringency conditions, moderate stringency conditions, or high stringency conditions are within the invention. Preferred such nucleotide acids are those having a nucleotide sequence that is the complement of all or a portion of SEQ ID NO: 1. Other variants of the native pprA gene within the invention are polynucleotides that share at least 65% (e.g., 65, 70, 75, 80, 85, 90, 91, 92, 93, 94, 95, 96, 97, 98, and 99%) sequence identity to SEQ ID NO: 1 or the complement of SEQ ID NO: 1 Nucleic acids that hybridize under stringent conditions to or share at least 65% sequence identity with SEQ ID NO: 1 or the complement of SEQ ID NO 1 can be obtained by techniques known in the art such as by making mutations in the native PprA gene, or by isolation from an organism expressing such a nucleic acid (e.g., an allelic variant). In a similar manner, nucleic acids that hybridize under stringent conditions to the nucleic acid of SEQ ID NO: 2 or the complement of SEQ ID NO: 2 can also be used in the invention.

Nucleic acid molecules encoding PprA or PprB fusion proteins are also within the invention. Such nucleic acids can be made by preparing a construct (e.g., an expression vector) that expresses a PprA or PprB fusion protein when introduced into a suitable host. For example, such a construct can be made by ligating a first polynucleotide encoding a PprA or PprB protein fused in frame with a second polynucleotide encoding another protein (e.g., a detectable label) such that expression of the construct in a suitable expression system yields a fusion protein.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups such as peptides (e.g., for targeting host cell receptors in vivo), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. USA 84:648-652; PCT Publication No. WO88/09810, published Dec. 15, 1988), hybridization-triggered cleavage agents. (See, e.g., Krol et al. (1988) BioTechniques 6:958-976) or intercalating agents. (See, e.g, Zon (1988) Pharm. Res. 5:539-549). To this end, the oligonucleotides may be conjugated to another molecule, e.g., a peptide, hybridization triggered cross-linking agent, transport agent, hybridization-triggered cleavage agent, etc.

Using the nucleotide of the native pprA or pprB gene and the amino acid sequence of a native PprA or PprB protein, those skilled in the art can create nucleic acid molecules that have minor variations in their nucleotide sequence, by, for example, standard nucleic acid mutagenesis techniques or by chemical synthesis. Variant pprA or pprB nucleic acid molecules can be expressed to produce variant PprA or PprB proteins.

Probes and Primers

The invention also includes oligonucleotide probes (i.e. isolated nucleic acid molecules conjugated with a detectable label or reporter molecule, e.g. a radioactive isotope, ligand, chemiluminescent agent or enzyme), and oligonucleotide primers (i.e. isolated nucleic acid molecules that can be annealed to a complementary target DNA by nucleic acid hybridization to form a hybrid between the primer and the target DNA strand, then extended along the target DNA by a polymerase, e.g. a DNA polymerase). Primer pairs can be used for amplification of a nucleic acid sequence, e.g. by the polymerase chain reaction (PCR) or other conventional nucleic acid amplification methods. Probes and primers within the invention are generally 15 nucleotides or more in length, preferably 20 nucleotides or more, more preferably 25 nucleotides and most preferably 30 nucleotides or more. Preferred probes and primers are those that hybridize to the native pprA or pprB gene sequences under high stringency conditions, and those that hybridize with pprA or pprB gene homologs under at least moderate stringency conditions. Preferably, probes and primers according to the present invention have complete sequence identity with the native pprA or pprB gene sequences, although probes differing from the native pprA or pprB gene sequences and that retain the ability to hybridize to native pprA or pprB gene sequences under stringent conditions may be designed by conventional methods.

PprA/PprB Proteins

In other aspects, the present invention utilizes a purified PprA protein encoded by the nucleic acid of the invention identified as SEQ ID NO: 1 (e.g., the polypeptide of SEQ ID NO:3), and a purified PprB protein encoded by the nucleic acid of the invention designated by SEQ ID NO: 2 (e.g., the polypeptide of SEQ ID NO:4). Variants of native PprA or PprB proteins such as fragments, analogs and derivatives of native PprA or PprB are also within the invention. Such variants include, e.g., a polypeptide encoded by a naturally occurring allelic variant of native gene, a polypeptide encoded by a homolog of a native gene, pprA or pprB and a polypeptide encoded by a non-naturally occurring variant of native pprA or pprB gene.

PprA or PprB protein variants have a peptide sequence that differs from a native PprA or PprB protein in one or more amino acids. The peptide sequence of such variants can feature a deletion, addition, or substitution of one or more amino acids of a native PprA or PprB polypeptide. Amino acid insertions are preferably of about 1 to 4 contiguous amino acids, and deletions are preferably of about 1 to 10 contiguous amino acids. In some applications, variant PprA or PprB proteins substantially maintain a native PprA or PprB protein functional activity (e.g., regulation of bacterial membrane permeability). For other applications, variant PprA or PprB proteins lack or feature a significant reduction in a PprA or PprB protein functional activity. Where it is desired to retain a functional activity of native PprA or PprB protein, preferred PprA or PprB protein variants can be made by expressing nucleic acid molecules within the invention that feature silent or conservative changes. Variant PprA or PprB proteins with substantial changes in functional activity can be made by expressing nucleic acid molecules within the invention that feature less than conservative changes.

PprA or PprB protein fragments corresponding to one or more particular motifs and/or domains or to arbitrary sizes, for example, at least 5, 10, 25, 30, 40, 50, 50, 70, 75, 80, 90, and 100 amino acids in length are within the scope of the present invention. Isolated peptidyl portions of PprA or PprB proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a PprA or PprB protein of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of native PprA or PprB protein.

Another aspect of the present invention concerns recombinant forms of the PprA or PprB proteins. Recombinant polypeptides preferred by the present invention, in addition to native PprA or PprB protein, are encoded by a nucleic acid that has at least 85% sequence identity (e.g., 85, 86, 87, 88, 89, 90, 91, 92, 93, 94, 95, 96, 97, 98, 99, 100%) with the nucleic acid sequence of SEQ ID NO: 1 for PprA and with nucleic acid sequence of SEQ ID NO: 2 for PprB. In a preferred embodiment, variant PprA or PprB proteins have one or more functional activities of native PprA or PprB proteins.

PprA or PprB protein variants can be generated through various techniques known in the art. For example, PprA or PprB protein variants can be made by mutagenesis, such as by introducing discrete point mutation(s), or by truncation. Mutation can give rise to a PprA or PprB protein variant having substantially the same, or merely a subset of the functional activity of a native PprA or PprB protein. Alternatively, antagonistic forms of the protein can be generated which are able to inhibit the function of the naturally occurring form of the protein, such as by competitively binding to another molecule that interacts with a PprA or PprB protein. In addition, agonistic forms of the protein may be generated that constitutively express one or more PprA or PprB functional activities. Other variants of PprA or PprB that can be generated include those that are resistant to proteolytic cleavage, as for example, due to mutations which alter protease target sequences. Whether a change in the amino acid sequence of a peptide results in a PprA or PprB protein variant having one or more functional activities of native PprA or PprB protein can be readily determined by testing the variant for a native PprA or PprB protein functional activity.

As another example, PprA or PprB protein variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential PprA or PprB protein sequences. The synthesis of degenerate oligonucleotides is well known in the art (see for example, Narang, SA (1983) Tetrahedron 39:3; Itakura et al. (1981) Recombinant DNA, Proc 3rd Cleveland Sympos. Macromolecules, ed. A G Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) Proc. Natl. Acad. Sci. USA 89:2429-2433; Devlin et al. (1990) Science 249:404-406; Cwirla et al. (1990) Proc. Natl. Acad. Sci. USA 87:6378-6382; as well as U.S. Pat. Nos. 5,223,409; 5,198, 346; and 5,096,815).

The invention also provides for reduction of PprA or PprB proteins to generate mimetics, e.g. peptide or non-peptide agents, that are able to disrupt binding of a PprA or PprB protein to other proteins or molecules with which a native PprA or PprB protein interacts. The mutagenic techniques described can also be used to map which determinants of a PprA or PprB protein participate in protein-protein interactions involved in, for example, binding of a PprA or PprB protein to each other or to other proteins which may function upstream (including both activators and repressors of its activity) of the PprA or PprB protein or to proteins or nucleic acids which may function downstream of the PprA or PprB protein, and whether such molecules are positively or negatively regulated by the PprA or PprB protein. To illustrate, the critical residues of a PprA or PprB protein which are involved in molecular recognition of, for example, a molecule having a moiety that binds the PprA or PprB protein can be determined and used to generate PprA or PprB protein-derived peptidomimetics which competitively inhibit binding of PprA or PprB protein with that moiety. By employing, for example, scanning mutagenesis to map the amino acid residues of a PprA or PprB protein that are involved in binding other proteins, peptidomimetic compounds can be generated which mimic those residues of native PprA or PprB protein. Such mimetics may then be used to interfere with the normal function of a PprA or PprB protein. For instance, non-hydrolyzable peptide analogs of such residues can be generated using benzodiazepine (e.g., see Freidinger et al. in Peptides: Chemistry and Biology, G.

R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J. Med. Chem. 29:295; and Ewenson et al. in Peptides: Structure and Function (Proceedings of the 9th American Peptide Symposium) Pierce Chemical Co. Rockland, Ill, 1985), _eta-turn dipeptide cores (Nagai et al. (1985) Tetrahedron Lett 26:647; and Sato et al. (1986) J. Chem. Soc. Perkin. Trans. 1:1231), and b-aminoalcohols (Gordon et al. (1985) Biochem. Biophys. Res. Commun. 126:419; and Dann et al. (1986) Biochem. Biophys. Res. Commun. 134:71). PprA or PprB proteins may also be chemically modified to create PprA or PprB derivatives by forming covalent or aggregate conjugates with other chemical moieties, such as glycosyl groups, lipids, phosphate, acetyl groups and the like. Covalent derivatives of PprA or PprB protein can be prepared by linking the chemical moieties to functional groups on amino acid side chains of the protein or at the N-terminus or at the C-terminus of the polypeptide.

The present invention further pertains to methods of producing the subject PprA or PprB proteins. For example, a host cell transfected with a nucleic acid vector directing expression of a nucleotide sequence encoding the subject polypeptides can be cultured under appropriate conditions to allow expression of the protein to occur. The cells may be harvested, lysed and the protein isolated. Recombinant PprA or PprB protein can be isolated from host cells using techniques known in the art for purifying proteins including ion-exchange chromatography, ultrafiltration, electrophoresis, and immunoaffinity with antibodies specific for such protein.

For example, His-tagged PprA or PprB proteins can be expressed in a cell such as *E. coli*. PCR products may be amplified for PprA or PprB using appropriate primer pairs, followed by cloning of the products into vectors such as pQE32 and pQE31. The vectors are transfected into *E. coli* strain M15, and PprA or PprB overproduction of the proteins is induced in the cells. The His-tagged proteins are subsequently purified from the cell extracts using a Ni-agarose column.

Alternatively, after PprA or PprB protein has been expressed in a cell, it can be isolated using any immuno-affinity chromatography. For instance, an anti-PprA or PprB antibody (e.g., produced as described below) can be immobilized on a column chromatography matrix, and the matrix can be used for immuno-affinity chromatography to purify PprA or PprB protein from cell lysates by standard methods (see, e.g., Ausubel et al., supra). After immuno-affinity chromatography, PprA or PprB protein can be further purified by other standard techniques, e.g., high performance liquid chromatography (see, e.g., Fisher, Laboratory Techniques In Biochemistry And Molecular Biology, Work and Burdon, eds., Elsevier, 1980). In another embodiment, PprA or PprB protein is expressed as a fusion protein containing an affinity tag (e.g., GST) that facilitates its purification.

PprA-or PprB-Protein Specific Antibodies

PprA or PprB proteins (or immunogenic fragments or analogs thereof) can be used to raise antibodies useful in the invention. For example, PprA or PprB proteins can be coupled to a carrier protein, such as KLH, as described in Ausubel et al., supra, mixed with an adjuvant, and injected into a host animal. Antibodies produced in that animal can then be purified by peptide antigen affinity chromatography. In particular, various host animals can be immunized by injection with a PprA or PprB protein or an antigenic fragment thereof.

Antibodies within the invention include polyclonal antibodies, monoclonal antibodies, single chain antibodies, Fab fragments, F(ab')$_2$ fragments, and molecules produced using a Fab expression library. Monoclonal antibodies (mAbs), which are homogeneous populations of antibodies to a particular antigen, can be prepared using the PprA or PprB proteins described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, mAbs can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77-96, 1983). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Once produced, polyclonal or monoclonal antibodies can be tested for specific PprA or PprB recognition by Western blot or immunoprecipitation analysis by standard methods, for example, as described in Ausubel et al., supra. Antibodies that specifically recognize and bind to PprA or PprB are useful in the invention. For example, such antibodies can be used in an immunoassay to monitor the level of PprA or PprB produced by a cell. Preferably, PprA or PprB protein selective antibodies of the invention are produced using fragments of the PprA or PprB protein that lie outside highly conserved regions and appear likely to be antigenic, by criteria such as high frequency of charged residues.

The antibodies of the invention can be used, for example, in the detection of PprA or PprB protein in a biological sample. Antibodies also can be used in a screening assay to measure the effect of a candidate compound on expression or localization of PprA or PprB protein. Additionally, such antibodies can be used to interfere with the interaction of PprA or PprB protein and other molecules that bind PprA or PprB protein.

Proteins that Associate with PprA or PprB

The invention also features methods for identifying polypeptides that can associate with a PprA or PprB protein. Any method that is suitable for detecting protein-protein interactions can be employed to detect polypeptides that associate with a PprA or PprB protein. Among the traditional methods that can be employed are co-immunoprecipitation, crosslinking, and co-purification through gradients or chromatographic columns of cell lysates or proteins obtained from cell lysates and the use of a PprA or PprB protein to identify proteins in the lysate that interact with a PprA or PprB protein. For these assays, the PprA or PprB protein can be a full length PprA or PprB protein, a particular domain of a PprA or PprB protein, or some other suitable PprA or PprB protein. Once isolated, such an interacting protein can be identified and cloned and then used, in conjunction with standard techniques, to alter the activity of the PprA or PprB protein with which it interacts. For example, at least a portion of the amino acid sequence of a protein that interacts with PprA or PprB protein can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel et al., supra; and Innis et al., supra).

Additionally, methods can be employed that result directly in the identification of genes that encode proteins that interact with a PprA or PprB protein. These methods include, for example, screening expression libraries, in a manner similar to the well known technique of antibody probing of λgt11 libraries, using a labeled PprA or PprB protein or a PprA or PprB fusion protein, for example, a PprA or PprB protein or domain fused to a marker such as an enzyme, fluorescent dye, a luminescent protein, or to an Ig Fc domain. There are also methods available that can detect protein-protein interaction in vivo. For example, as described herein the two-hybrid system can be used to detect such interactions in vivo. See, e.g., Chien et al., Proc. Natl. Acad. Sci. USA 88:9578, 1991. Briefly, as one example of utilizing such a system, plasmids are constructed that encode two hybrid proteins: one plasmid includes a nucleotide sequence encoding the DNA-binding domain of a transcription activator protein fused to a nucleotide sequence encoding a native PprA or PprB protein, a PprA or PprB protein variant, or a PprA or PprB fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. For example, a PprA or PprB protein may be used as the bait. Total genomic or cDNA sequences are fused to the DNA encoding an activation domain. This library and a plasmid encoding a hybrid of a bait PprA or PprB protein fused to the DNA-binding domain are co-transformed into a yeast reporter strain, and the resulting transformants are screened for those that express the reporter gene. For instance, a bait PprA or PprB gene sequence, such as that encoding PprA or PprB protein or a domain of PprA or PprB protein can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with a bait PprA or PprB protein are to be detected can be made using methods routinely practiced in the art. According to the particular system described herein, for example, the cDNA fragments can be inserted into a vector such that they are translationally fused to the transcriptional activation domain of GAL4. This library can be co-transformed along with the PprA- or PprB -GAL4 encoding fusion plasmid into a yeast strain which contains a lacZ gene driven by a promoter which contains GAL4 activation sequence. A cDNA encoded protein, fused to GAL4 transcriptional activation domain, that interacts with bait PprA or PprB protein will reconstitute an active GAL4 protein and thereby drive expression of the HIS3 gene. Colonies that express HIS3 can then be purified from these strains and used to produce and isolate bait PprA or PprB protein-interacting proteins using techniques routinely practiced in the art.

Detection of PprA or PprB Polynucleotides and Proteins

The invention encompasses methods for detecting the presence of a PprA or PprB protein or a pprA or pprB nucleic acid in a biological sample as well as methods for measuring the level of a PprA or PprB protein or a pprA or pprB nucleic acid in a biological sample.

A preferred agent for detecting a nucleic acid encoding a PprA or PprB protein is a labeled nucleic acid probe capable of hybridizing (e.g., under stringent hybridization conditions) to the nucleic acid encoding the PprA or PprB protein. The nucleic acid probe can be, for example, all or a portion of the native pprA or pprB gene itself (e.g., a nucleic acid molecule having the sequence of SEQ ID NO: 1 or SEQ ID NO: 2 or all or a portion of a complement of the native pprA or pprB gene. Similarly, the probe can also be all or a portion of a pprA or pprB gene variant, or all or a portion of a complement of a pprA or pprB gene variant. For instance, oligonucleotides at least 15, 30, 50, 75, 100, 125, 150, 175, 200, 225, or 250 nucleotides in length that specifically hybridize under stringent conditions to the native pprA or pprB gene or a complement of the native pprA or pprB gene can be used as probes within the invention. A preferred agent for detecting a PprA or PprB protein is an antibody capable of binding to a PprA or PprB protein, preferably an antibody with a detectable label.

Detection methods of the invention can be used to detect an mRNA encoding a PprA or PprB protein, a genomic DNA encoding a PprA or PprB protein, or a PprA or PprB protein in a biological sample in vitro as well as in vivo. For example, in vitro techniques for detection of mRNAs encoding a PprA or PprB protein include Northern hybridizations and in situ hybridizations. In vitro techniques for detection of a PprA or PprB protein include enzyme linked immunosorbent assays (ELISAs), Western blots, immunoprecipitations and immunofluorescence. In vitro techniques for detection of genomic DNA encoding a PprA or PprB protein include Southern hybridizations. In vivo techniques for detection of a PprA or PprB protein include introducing a labeled anti-PprA or anti-PprB antibody into a biological sample or test subject. For example, the antibody can be labeled with a radioactive marker whose presence and location in a biological sample or test subject can be detected by standard imaging techniques.

Screening for Genes Regulated by pprA/pprB

The invention also encompasses methods for identifying genes that are under the regulation of the PprA/PprB complex. Such genes are likely to be involved in aspects of control of membrane permeability to antibiotics, and as such will provide important new targets for development of novel anti-microbials. Gene array analysis is a powerful strategy well known in the art for discovery of genes involved in a particular biological process. Comparison of the profiles of the multitude of genes that are expressed by cells under particular biological conditions, with identification of subsets of genes that are differentially expressed in one condition and not another, leads to the discovery of previously unappreciated correlations of specific gene activity associated with particular biological processes. To facilitate discovery of genes controlling permeability of bacterial cell membranes, a cell line having normal permeability to antibiotics may be compared with one having decreased permeability. For example, analysis of the gene expression profiles in cells manipulated to overexpress pprA/pprB, as compared with normally expressing cells, may be used to reveal downstream genes whose expression is under the regulation of pprA/pprB.

Screening for Chemicals that Increase Bacterial Membrane Permeability

An important unmet need is the development of antibiotics to combat new generations of multi-drug resistant bacteria. As a means of identifying chemical compounds capable of altering bacterial membrane permeability, a further embodiment of the invention encompasses screening of chemical libraries for discovery of compounds with the ability to cause detectable changes in the expression of the pprA/pprB genes in response to contact with specific chemical entities. For example, a pprA/pprB construct combined with one of the well known reporter systems can be used to screen for detection of chemicals that stimulate expression of pprA/pprB. Chemicals shown to cause upregulation of these genes and a corresponding increase in cell membrane permeability could be identified and used to improve penetration of antibiotics into drug resistant bacteria.

EXAMPLES

The present invention is further illustrated by the following specific examples which not to be construed as limiting the scope or content of the invention in any way.

Example 1

A mutant *P. aeruginosa* (PAK) strain was used to identify the pprA membrane permeability-associated gene. Spontaneous neomycin resistant mutants of PAK were selected by culturing on L-agar medium containing 200 µg/ml neomycin. One neomycin-resistant isolate, designated PAK1-3, also displayed increased resistance to other antibiotics including aminoglycosides (kanamycin, streptomycin, gentamicin, amikacine and tobamycin), ciprofloxacin, and erythromycin (Table 1). PAK1-3 exhibited a slower growth rate compared to its parent strain PAK, as seen from smaller colony sizes and delayed increase in cell density in liquid cultures. Its sensitivity to carbenicillin was not significantly changed.

Example 2

A gene associated with membrane permeability, termed pprA, was identified by complementation assay in PAK1-3 cells. On the assumption that the PAK1-3 strain is an impermeable mutant due to loss of a gene function, an effort was made to complement the mutant with wild type PAK chromosomal DNA clones. A clone bank of 3-5 kb PAK chromosomal DNA was constructed in pUCP18, a broad host range plasmid with a lac promoter and β-lactamase. Plasmids with DNA inserts were gel purified from the clone bank and electroporated into PAK1-3.

Transformants were first selected on L-agar containing carbenicillin (150 µg/ml) and then replica plated on L-agar containing carbenicillin (150 µg/ml) plus neomycin (200 µg/ml) to screen for isolates that are sensitive to aminoglycosides. Of the 5,000 colonies screened, three showed sensitivity to neomycin. Plasmids were purified from the three isolates and re-transformed into fresh PAK1-3 cells. Two of the three plasmids conferred sensitivity to the aminoglycosides on PAK1-3 cells. DNA sequence analysis of the effective two plasmids showed that they were identical. This plasmid was designated pUCP18B.

Plasmid pUCP18B contains a 3,280 base pair (bp) DNA insert, encoding a 2,768 bp long putative histidine kinase homolog (PA4293), designated pprA, (SEQ ID NO:1) which is transcriptionally fused under the lac promoter of the vector. Other studies (testing of subclones derived and insertional inactivation of the histidine kinase structural gene in pUCP18B) demonstrated that expression of the pprA gene was essential to confer aminoglycoside sensitivity to the strain PAK1-3. The protein encoded by the pprA gene (PprA) is likely a cytoplasmic protein as it lacks a signal sequence or trans-membrane segments. The N-terminus of PprA harbors PAS and PAC motifs, motifs involved in various signal sensing functions. Zhulin et al., 1997, Trends Biochem Sci. 22 (9): 331-3.

Example 3

An additional gene associated with bacterial membrane permeability was identified. The 827 bp long putative response regulator (PA4296), which was named pprB (SEQ ID NO: 2), resides 1,184 bp upstream of the pprA gene and is transcribed in the opposite direction than that of pprA.

The pprB gene was amplified from the PAK chromosome by PCR and cloned into pUCP19, inserted in the same or opposite direction relative to the lac promoter on the vector. The resulting constructs were designated pZLRR-α and pZLRR-β, respectively. See, Wang et al., 2003, Antimicrobial Agents and Chemotherapy 47:95-101. The PCR product was cloned into pCR2.1-TOPO, resulting pCR-RR in which the pprB gene is in the opposite direction relative to the lac promoter. The pprB gene was then subcloned as EcoRI fragment into the same site of pUCP19, inserting the pprB gene in the same or opposite direction relative to the lac promoter, designated pZLRR-α and pZLRR-β, respectively. A tetracycline-resistance gene cassette was isolated from pBR322 as an EcoRI-AvaI fragment, blunt-ended, and inserted into the SspI and ScaI sites of pUCP19 to generate pUCPT19. The EcoRI fragment from the pCR-RR, which contains the pprB gene, was inserted into the same site of pUCPT19 to generate pRRBTc, in which the pprB is in the same direction as the lac promoter.

Experiments were performed to determine whether increased expression of pprB could also confer sensitivity to aminoglycosides to PAK1-3 cells. The plasmids pZLRR-α and pZLRR-β were transferred into PAK1-3 cells. Only pZLRR-α, but not pZLRR-β conferred sensitivity to aminoglycosides. The effect of PprB overexpression was much more dramatic than PprA overexpression on the MIC change of PAK1-3 (Table 1).

Example 4

PprA or PprB were purified and expressed at high levels in *E. coli*. To produce PprA or PprB in *E.coli*, coding regions of the two open reading frames were amplified by PCR as described in Wang et al., supra. The PCR products were first cloned into pCR2.1-TOPO, designated pYW017 and pYW020, respectively. Subsequently, a 2.8 kb pprA fragment from pYW017 and an 862 bp pprB fragment from pYW020 were isolated and subcloned into the BamHI and HindIII sites of pQE32 and pQE31, resulting in pYW021 and pYW024, respectively.

To purify the His-tagged PprA or PprB, *E.coli* strain M15 harboring pREP4 and pYW021 or pYW024 were induced with 1 mM IPTG for six hours at 28° C. His-tagged PprA and PprB were affinity purified using Ni-agarose column from the soluble fraction of the cell extracts according to the protocol provided by Qiagen, Inc. The purified proteins were dialyzed against storage buffer (50 mM TrisCl pH8.0, 50 mM KCl, 5 mM MgCl$_2$, 1 mM DTT and 50% glycerol) for overnight and stored at–20° C. until use.

Example 5

PprA and PprB function in a two-component regulatory system. Like other two-component regulatory genes, both PprA and PprB contain conserved phosphorylation sites (histidine and aspartate, respectively). An in vitro phosphorylation assay was performed to investigate the relationship between the PprA and PprB. PprA and PprB were purified as described in Example 4. Ten µl of reaction buffer [50 mM TrisCl pH7.4, 50 mM KCl, 5 mM MgCl2, 1 mM DTT] containing 5 µCi of [γ-$^{32}$P] ATP was mixed with 5 µl of each purified protein and incubated at room temperature for 5 minutes. The reaction was terminated by adding 5 µl of 4× loading buffer. The resulting reaction mixture was subjected to SDS-PAGE, stained with Coomassie Blue, dried, and exposed to X-ray film. PprA was phosphorylated; PprB was not. Notably, however, when PprA was mixed with PprB, PprB became highly phosphorylated. Thus, PprA functions as a specific kinase for PprB.

Example 6

Bacterial strains PAK and PAK1-3 were subjected to a membrane permeability assay. A whole-cell alkaline phosphatase assay was derived from a membrane-diffusion barrier model in *E. coli*. Martinez et al., 1992, Biochemistry. 31 (46): 11500-9. In this model, alkaline phosphatase displayed two types of kinetics.

Growth of the PAK and PAK1-3 in L-broth produced undetectable levels of alkaline phosphatase activity whereas growth in low phosphate media resulted in high levels of alkaline phosphatase activities. However, under the low phosphate condition, a high degree of cell lysis was observed, which interfered with the assay. To overcome this, a plasmid that constitutively expresses the alkaline phosphatase gene, pWC005, was introduced into both PAK and PAK1-3. To generate pWC005, a 0.5 kb NdeI-XmnI DNA fragment from pUCP19, encoding the bla gene promoter and N-terminal signal sequence, was ligated into the SamI site of pSOP3 which is located upstream of a signal sequenceless alkaline phosphatase structural gene. Ouchane et al., 1999, J Biol Chem. 274 (24): 17290-6. The resulting pWC005 encodes a translational fusion between the bla signal sequence and alkaline phosphatase.

The resulting strains containing the introduced pWC005 were grown in L-broth and incubated with low concentration of para-nitrophenyl phosphate (pNPP, 0.1 mg/ml) which measures pNPP diffusion mediated alkaline phosphatase activity. The alkaline phosphatase substrate permeation assay was performed as follows. Overnight cultures of *P. aeruginosa* with proper antibiotics were washed once with fresh LB and re-inoculated into 3 ml of fresh LB medium without antibiotics to about $A_{600}$=0.1. After culturing for 7 hours, cells were washed once with ice-cold reaction buffer (0.1M of Tris-HCl, pH 8.0, 100 mM NaCl, 5 mM MgCl$_2$, and 0.1 mM ZnCl$_2$), resuspended in 3 ml of the same buffer and the final cell density ($A_{600}$) was measured. The reaction was started by adding 0.1 ml of the cell suspension into a reaction mixture containing 0.8 ml of reaction buffer and 0.1 ml of 0.08 mg/ml pNPP in 1 M Tris-HCl (pH 8.0). All reactions were carried out in a standard plastic spectrophotometer cuvette at room temperature. Samples were allowed to react for 2 minutes and 0.1 ml of 1 M KH$_2$PO$_4$ was added to terminate the reaction. Cells were centrifuged and the $A_{410}$ of the supernatant was measured. Samples with no substrate were used as negative controls. The index of outer-membrane permeability was calculated as: Pm=$A_{410}$/$A_{600}$.

Referring to FIG. 1, membrane permeability in PAK and control and pZLRR-α transfected PAK1-3 cells was compared. Outer-membrane permeability (Pm) of PAK1-3 was at least 30% lower than that of wild type PAK. When the pprB expressing plasmid, pZLRR-α was introduced into PAK1-3, the membrane permeability of the resulting strain was much higher than in PAK1-3 harboring vector alone.

Example 7

Overexpression of the pprB gene in clinical isolates increases sensitivity to aminoglycosides. The pprB overexpresser construct was introduced into aminoglycoside-resistant clinical isolates of *P. aeruginosa*. 18 cystic fibrosis (CF) isolates and 18 non-CF blood isolates showing varying degrees of resistance to all aminoglycosides were randomly chosen for analysis. Since most of the strains were also resistant to carbenicillin, but sensitive to tetracycline (100 µg/ml), a tetracycline-resistant construct, pRRBTc, that expresses the pprB gene under lac promoter was used. The plasmid was introduced into 17 isolates by electroporation and 14 of those transformants, resulted in decreased MIC to aminoglycosides in the presence of the pRRBTc, compared to those containing pUCPT19 vector alone (Table 2).

Example 8

The pprA/pprB system may be used to identify potential new target genes or proteins for design of novel antibiotics. These genes, or cells expressing varying levels of these genes, may be incorporated in a gene array strategy designed to reveal presently unknown targets involved in membrane permeability. For example, such a gene array approach has been used in *P. aeruginosa* to reveal a number of inner and outer membrane proteins under regulation of the pprA/pprB genes.

Total bacterial RNAs are isolated from both wild type PAK and the pprB mutant strain, and cDNAs are then generated by random reverse transcription while labeling with either fluorescent dye Cy3 or Cy5. Cy3-labeled probe from PAK is mixed with Cy5-labeled probe of pprB mutant while Cy3 labeled probe of pprB mutant is mixed with Cy5 labeled probe of PAK. The two mixed sets of probes are each used to hybridize with DNA chips, either DNA spotted microarray or oligonucleotide chip from Affymetrix (Santa Clara, Calif.). Relative abundance of the transcript from each gene on the genome of *P. aeruginosa* is compared by comparing the normalized intensities of the two fluorescent dyes on the same spot. The proteins encoded by the genes, if involved in the control of membrane permeability to antibiotics, are new targets for design of novel antibiotics.

Example 9

To identify a gene that is regulated by PprA/PprB, the gene promoter is fused with a reporter gene such as lacZ or gfp. The fusion construct is introduced into *P. aeruginosa* and used to screen chemicals that can alter the expression of the reporter genes. The PprA/PprB responsive genes can be identified using a number of techniques including gene chip technology to identify genes that are down or up regulated in an pprB mutant background compared to that of wild type strain.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

What is claimed is:

1. A method of increasing sensitivity of an antibiotic resistant bacterium to an antibiotic comprising:
   administering to an antibiotic resistant bacterium an isolated nucleic acid comprising the polynucleotide sequence of SEQ ID NO:1 and encoding a PprA polypeptide; and,
   modulating in a bacterium expression of a PprA polypeptide; and,
   increasing the membrane permeability of an antibiotic resistant bacterium; thereby,
   increasing the sensitivity of an antibiotic resistant bacterium to an antibiotic.

2. The method of claim 1, wherein the step of modulating levels of the PprA polypeptide comprises introducing into the antibiotic resistant bacterium a nucleic acid encoding the polypeptide.

3. The method of claim 2, wherein the nucleic acid encodes an amino acid sequence identified by SEQ ID NO: 3.

4. The method of claim 1, wherein the bacterium is a *Pseudomonas aeruginosa* bacterium.

5. The method of claim 1, wherein the step results in a change in membrane permeability in the bacterium.

6. The method of claim 1, wherein the antibiotic administered to the antibiotic resistant bacterium is an aminoglycoside.

7. A bacterium into which has been introduced a vector encoding a nucleic acid sequence identified by SEQ ID NO: 1 that modulates in the bacterium expression of a PprA polypeptide.

8. The bacterium of claim 7, wherein the vector expresses the polypeptide identified by SEQ ID NO: 3.

9. The bacterium of claim 8, wherein the polypeptide is PprA.

10. The bacterium of claim 7, wherein the bacterium is a *Pseudomonas aeruginosa* bacterium.

11. A vector comprising a promoter operably linked to a nucleic acid encoding a PprA polypeptide.

12. The vector of claim 11, wherein the nucleic acid comprises the polynucleotide sequence of SEQ ID NO:1.

* * * * *

UNITED STATES PATENT AND TRADEMARK OFFICE
CERTIFICATE OF CORRECTION

| | |
|---|---|
| PATENT NO. | : 7,271,005 B2 |
| APPLICATION NO. | : 10/425241 |
| DATED | : September 18, 2007 |
| INVENTOR(S) | : Shouguang Jin et al. |

It is certified that error appears in the above-identified patent and that said Letters Patent is hereby corrected as shown below:

Col. 1, line 11
In the section, STATEMENT AS TO FEDERALLY FUNDED RESEARCH, replace "The United States government may have certain rights in the invention" with --The United States government has certain rights in the invention--

Signed and Sealed this

First Day of April, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 2769
<212> TYPE: DNA
<213> ORGANISM: Pseudomonas aeruginosa

<400> SEQUENCE: 1

```
atgttcgaat tttcccgctc gtcgtccgcc gaggccgaga ggccggaacc cttttcgcag     60
gaaggccccg ccctctggag cgcttcgctg aggagttggg acctgtgctt cgagatggac    120
gaacaggacc gcgtgatccg ggtcggcggg cggcaggcgt atcgtctgca gtgcgcccat    180
gggcttggcg aacagccgcg gcctttcgcc gagtatctgg agcggcgcgc ccccggtgcc    240
ccgacgctgg ccggcctgcg ccggggcgag cgtctcgacc tgacgctgcg cagcgatgcc    300
gccgcgccat tgacctgtcg tttccagccg atgcagccgc tcgacggcct gggacgctcg    360
ctgctgttgg gcatggacat ctccgacctc aactggcagt ccgacagcca gcagcaccag    420
ttgcagagcc tgagcctggg caagctgatc cttttcgcgtc tgcgccatgt ctcccacggg    480
cacctggcgg aggcggtcca ggagattctc gaatcgctct ccggcgcgtt ccagatgcag    540
gctatcgccc tgctgctggg cgacggcaag ggcttctgca cggtcttcgc cagtcatgtg    600
cggcctggca gtgacagttt gctgcgaccg cccctgcaac tcgccgacga cgatctgcgt    660
gaaggggcgg gcgcgcgctt gctacgccgt ggcgaaggcg cctcgacgct gctccggcag    720
attggcgagg acgcgctcta cctggtgccg gcgacgatgc gcggtggccg cctggggggcg    780 ttgctggtcc ggccgatgtc gctggagcag ctcgcccagg ggcccgcgcc gcaggactgg    840
caatacctcg cggaactgct ggcgaaccag gtggcggacc gctgcgagct ccacgagcag    900
cacgacagtt cgcgcaagct ggggctgttg caggagatga tcggcggcgg ctggtggcgt    960
tactgggcgg agcaggaact cttcgaactg gcgccggcct tgcacgacag cctggggttg   1020
accggcgagt atcgtcgggt gccgctggaa cacctgcagg gcctgctgca accggcggac   1080
gccgacgagc tcggcctgcg cctgcgtgcc agcctgcgca gcggccaggc gctggcccag   1140
gacctttgcc tgcgtcagcc ggatagccgc ggcgagcgcc gctggctgcg catcgagggc   1200
cggccgctgg gacgcggcag tgccctgggg ctgtccggcg tgctgctcga catcagcgaa   1260
ggccggcgcc aggaggaacg ggcacaggcg gcccacgcgc ggttgcgcag cctgatcgac   1320
```

-continued

| | |
|---|---|
| agtgcgccgg tggtgatcta tgtccagcgg gtcgagcagg ggcacctggt gccggagttc | 1380 |
| tacagcgaaa gcgcgagcaa cctgctcggc ctcgacctgc agggacagag ttggcaggcg | 1440 |
| ctcgccgagc gggtgcatcc ggatgatctg gaggccttt tcgcccgcgg ccgcgagctg | 1500 |
| cttcgcgaag gccgggtgaa gacccgctat cgcctcgccg atggccaggg caactggcac | 1560 |
| tggctctacg acgaagccaa gctgctgcgc gatgcccagg gcctgcccag cgaggcggtg | 1620 |
| ggcctgtggc tggacgtgac cgagcagcac ctggcggcac agcgtatcgc cgagagcgag | 1680 |
| gaacgctacc gggtcctggt ggaggattcg ccggcgctga tctgtcgcta taccgccgac | 1740 |
| ctggtgctga cctacgtgaa ccggaccttc gccgatagcc tcgcgaccag cccggagcgc | 1800 |
| ctggtcggtc gccggctcga cgagtggctg gcggcggaag acgccagcgc cttgcgcgcg | 1860 |
| cgtctgctgg gttcgccgcg ggagggcgcc agcgaggtgc cggaactgcg cttcaacctg | 1920 |
| ccggggcaac gttttctctg gctggtgtgg gccgagcgac cgttgttcga cgcccggggc | 1980 |
| gaattgtgcg aggtacaggc ggtgggacgc gacaacacgc cggtgcgtcg ggcccagcag | 2040 |
| caactggcgc aaggcgccaa gatggccagc ctgggggaga tggtcagcgg cctcgcccac | 2100 |
| gaggtgaagc agccgctgca cgtgctgcgc atgaccctgt tcaacatgcg ccagcggatg | 2160 |
| aacagcgtcg gcctcgacgg cgactacctg ggcgagaaac tggagcgcat ggatgcccag | 2220 |
| gtcctgcgcg tcgaccgcct ggtcagtcac ctcggcgtgt tcagccgcaa gtcggcgctg | 2280 |
| gaggcgctgc cgttcgaccc ctatgccgcc ttcgaaggcg ccctgggcct gctcggcgag | 2340 |
| gggctgcgtc agcacgccat cgaggtagag tgcccggcgc cgacgcagcg gatggtggtg | 2400 |
| cgagggcagg cggaccagtt ggagcaggtg atcatcaacc tgctcgccaa cgcccgcgat | 2460 |
| gccctgctcg gcaatcccgg cctggccagc cggcgcgttc gcctggagca ggtggcctgc | 2520 |
| cgcgaaccgg gctgggtcga attgcacgtg cacgacaacg gcggcgggat agaaccgctc | 2580 |
| ctgctggagc ggatattcga acccttcttc accaccaagg cggagggcaa gggtaccggc | 2640 |
| ctgggtctct cggtcagcca cgatctggtg cgcaacatgg gcggtagcct gacggcggcc | 2700 |
| aaccaggggg aggtgcgtt gttcgtggtt cgcttgccgc tggcggcgcc cgccgaggcg | 2760 |
| ggcggatga | 2769 |

<210> SEQ ID NO 2
<211> LENGTH: 828
<212> TYPE: DNA
<213> ORGANISM: Pseudomonas aeruginosa

<400> SEQUENCE: 2

| | |
|---|---|
| atggacaaac cggcctcgcg gcatttcagc gtcttgatca tcgatgatga accccaggtg | 60 |
| acctcggaac tccgcgaact gctggaaaac agtggctacc gttgcgtaac cagcaccccac | 120 |
| cgggagtcgg cgatcgccag cttccaggcc gacccgaaca tcggcctggt catctgcgac | 180 |
| ctctacctgg gccaggacaa cggtatccgc ctgatcgaga gcctcaagga agtcgccggc | 240 |
| aacggcaggt tcttcgaatc gatcatcctc accggtcacg atggccgcca ggaagtgatc | 300 |
| gaggccatgc gggtcggcgc cgccgactac taccagaaac cggtggcgcc gcaggaactg | 360 |
| ctgcatggcc tcgaacgcct ggagagccgc ctgcacgagc gcgtccgcag ccagttgagc | 420 |
| ctgagccacg tcaaccagcg cctggaatac ctcgccgaat cgctgaactc gatctaccgc | 480 |
| gacatccaca gatcaagta cgaggtacac ggcaacagcc agccgagcgc cctcaggagc | 540 |
| gaagacagcc agccgtccgc gccgccggcg ccggtcgcgg aaagccaggt gtccccgagc | 600 |
| aatccgctgt tcggcaagct gtcgccccgc cagcaggcgg tggcgcggct ggtgagcaag | 660 |

-continued

```
ggcctgacca actaccagat agcctacgag ctgggcatca ccgagaacac ggtgaagctg    720
tacgtctccc aggtgctgcg cctgatgcat atgcacaacc gcacccagtt ggcgctggcc    780
ctgtcgcctg cggcgatgca gcagggcagc ggagcggtgg tgcactga                 828
```

```
<210> SEQ ID NO 3
<211> LENGTH: 922
<212> TYPE: PRT
<213> ORGANISM: Pseudomonas aeruginosa

<400> SEQUENCE: 3
```

| | | | | | | | | | | | | | | |
|---|---|---|---|---|---|---|---|---|---|---|---|---|---|---|
| Met | Phe | Glu | Phe | Ser | Arg | Ser | Ser | Ala | Glu | Ala | Glu | Arg | Pro | Glu |
| 1 | | | | 5 | | | | | 10 | | | | | 15 |
| Pro | Phe | Ser | Gln | Glu | Gly | Pro | Ala | Leu | Trp | Ser | Ala | Ser | Leu | Arg | Ser |
| | | | 20 | | | | | 25 | | | | | 30 | |
| Trp | Asp | Leu | Cys | Phe | Glu | Met | Asp | Glu | Gln | Asp | Arg | Val | Ile | Arg | Val |
| | | 35 | | | | | 40 | | | | | 45 | | |
| Gly | Gly | Arg | Gln | Ala | Tyr | Arg | Leu | Gln | Cys | Ala | His | Gly | Leu | Gly | Glu |
| | 50 | | | | | 55 | | | | | 60 | | | |
| Gln | Pro | Arg | Pro | Phe | Ala | Glu | Tyr | Leu | Glu | Arg | Arg | Ala | Pro | Gly | Ala |
| 65 | | | | | 70 | | | | | 75 | | | | | 80 |
| Pro | Thr | Leu | Ala | Gly | Leu | Arg | Arg | Gly | Glu | Arg | Leu | Asp | Leu | Thr | Leu |
| | | | | 85 | | | | | 90 | | | | | 95 | |
| Arg | Ser | Asp | Ala | Ala | Pro | Leu | Thr | Cys | Arg | Phe | Gln | Pro | Met | Gln |
| | | | 100 | | | | | 105 | | | | | 110 | |
| Pro | Leu | Asp | Gly | Leu | Gly | Arg | Ser | Leu | Leu | Gly | Met | Asp | Ile | Ser |
| | | 115 | | | | | 120 | | | | | 125 | | |
| Asp | Leu | Asn | Trp | Gln | Ser | Asp | Ser | Gln | Gln | His | Gln | Leu | Gln | Ser | Leu |
| | 130 | | | | | 135 | | | | | 140 | | | |
| Ser | Leu | Gly | Lys | Leu | Ile | Leu | Ser | Arg | Leu | Arg | His | Val | Ser | His | Gly |
| 145 | | | | | 150 | | | | | 155 | | | | | 160 |
| His | Leu | Ala | Glu | Ala | Val | Gln | Glu | Ile | Leu | Glu | Ser | Leu | Ser | Gly | Ala |
| | | | | 165 | | | | | 170 | | | | | 175 | |
| Phe | Gln | Met | Gln | Ala | Ile | Ala | Leu | Leu | Leu | Gly | Asp | Gly | Lys | Gly | Phe |
| | | | 180 | | | | | 185 | | | | | 190 | |
| Cys | Thr | Val | Phe | Ala | Ser | His | Val | Arg | Pro | Gly | Ser | Asp | Ser | Leu | Leu |
| | | 195 | | | | | 200 | | | | | 205 | | |
| Arg | Pro | Pro | Leu | Gln | Leu | Ala | Asp | Asp | Leu | Arg | Glu | Gly | Ala | Gly |
| | 210 | | | | | 215 | | | | | 220 | | | |
| Ala | Arg | Leu | Leu | Arg | Arg | Gly | Glu | Gly | Ala | Ser | Thr | Leu | Leu | Arg | Gln |
| 225 | | | | | 230 | | | | | 235 | | | | | 240 |
| Ile | Gly | Glu | Asp | Ala | Leu | Tyr | Leu | Val | Pro | Ala | Thr | Met | Arg | Gly | Gly |
| | | | | 245 | | | | | 250 | | | | | 255 | |
| Arg | Leu | Gly | Ala | Leu | Leu | Val | Arg | Pro | Met | Ser | Leu | Glu | Gln | Leu | Ala |
| | | | 260 | | | | | 265 | | | | | 270 | |
| Gln | Gly | Pro | Ala | Pro | Gln | Asp | Trp | Gln | Tyr | Leu | Ala | Glu | Leu | Leu | Ala |
| | | 275 | | | | | 280 | | | | | 285 | | |
| Asn | Gln | Val | Ala | Asp | Arg | Cys | Glu | Leu | His | Glu | Gln | His | Asp | Ser | Ser |
| | 290 | | | | | 295 | | | | | 300 | | | |
| Arg | Lys | Leu | Gly | Leu | Leu | Gln | Glu | Met | Ile | Gly | Gly | Trp | Trp | Arg |
| 305 | | | | | 310 | | | | | 315 | | | | | 320 |
| Tyr | Trp | Ala | Glu | Gln | Glu | Leu | Phe | Glu | Leu | Ala | Pro | Ala | Leu | His | Asp |
| | | | | 325 | | | | | 330 | | | | | 335 | |
| Ser | Leu | Gly | Leu | Thr | Gly | Glu | Tyr | Arg | Arg | Val | Pro | Leu | Glu | His | Leu |

-continued

```
                    340                 345                 350
Gln Gly Leu Leu Gln Pro Ala Asp Ala Asp Glu Leu Gly Leu Arg Leu
            355                 360                 365
Arg Ala Ser Leu Arg Ser Gly Gln Ala Leu Ala Gln Asp Leu Cys Leu
        370                 375                 380
Arg Gln Pro Asp Ser Arg Gly Glu Arg Arg Trp Leu Arg Ile Glu Gly
385                 390                 395                 400
Arg Pro Leu Gly Arg Gly Ser Ala Leu Gly Leu Ser Gly Val Leu Leu
                405                 410                 415
Asp Ile Ser Glu Gly Arg Arg Gln Glu Arg Ala Gln Ala Ala His
            420                 425                 430
Ala Arg Leu Arg Ser Leu Ile Asp Ser Ala Pro Val Val Ile Tyr Val
        435                 440                 445
Gln Arg Val Glu Gln Gly His Leu Val Pro Glu Phe Tyr Ser Glu Ser
450                 455                 460
Ala Ser Asn Leu Leu Gly Leu Asp Leu Gln Gly Gln Ser Trp Gln Ala
465                 470                 475                 480
Leu Ala Glu Arg Val His Pro Asp Asp Leu Glu Ala Phe Phe Ala Arg
                485                 490                 495
Gly Arg Glu Leu Leu Arg Glu Gly Arg Val Lys Thr Arg Tyr Arg Leu
            500                 505                 510
Ala Asp Gly Gln Gly Asn Trp His Trp Leu Tyr Asp Glu Ala Lys Leu
        515                 520                 525
Leu Arg Asp Ala Gln Gly Leu Pro Ser Glu Ala Val Gly Leu Trp Leu
    530                 535                 540
Asp Val Thr Glu Gln His Leu Ala Ala Gln Arg Ile Ala Glu Ser Glu
545                 550                 555                 560
Glu Arg Tyr Arg Val Leu Val Glu Asp Ser Pro Ala Leu Ile Cys Arg
                565                 570                 575
Tyr Thr Ala Asp Leu Val Leu Thr Tyr Val Asn Arg Thr Phe Ala Asp
            580                 585                 590
Ser Leu Ala Thr Ser Pro Glu Arg Leu Val Gly Arg Arg Leu Asp Glu
        595                 600                 605
Trp Leu Ala Ala Glu Asp Ala Ser Ala Leu Arg Ala Arg Leu Leu Gly
    610                 615                 620
Ser Pro Arg Glu Gly Ala Ser Glu Val Pro Glu Leu Arg Phe Asn Leu
625                 630                 635                 640
Pro Gly Gln Arg Phe Leu Trp Leu Val Trp Ala Glu Arg Pro Leu Phe
                645                 650                 655
Asp Ala Arg Gly Glu Leu Cys Glu Val Gln Ala Val Gly Arg Asp Asn
            660                 665                 670
Thr Pro Val Arg Arg Ala Gln Gln Leu Ala Gln Gly Ala Lys Met
        675                 680                 685
Ala Ser Leu Gly Glu Met Val Ser Gly Leu Ala His Glu Val Lys Gln
    690                 695                 700
Pro Leu His Val Leu Arg Met Thr Leu Phe Asn Met Arg Gln Arg Met
705                 710                 715                 720
Asn Ser Val Gly Leu Asp Gly Asp Tyr Leu Gly Glu Lys Leu Glu Arg
                725                 730                 735
Met Asp Ala Gln Val Leu Arg Val Asp Arg Leu Val Ser His Leu Gly
            740                 745                 750
Val Phe Ser Arg Lys Ser Ala Leu Glu Ala Leu Pro Phe Asp Pro Tyr
        755                 760                 765
```

```
Ala Ala Phe Glu Gly Ala Leu Gly Leu Leu Gly Glu Gly Leu Arg Gln
        770                 775                 780

His Ala Ile Glu Val Glu Cys Pro Ala Pro Thr Gln Arg Met Val Val
785                 790                 795                 800

Arg Gly Gln Ala Asp Gln Leu Glu Gln Val Ile Ile Asn Leu Leu Ala
                805                 810                 815

Asn Ala Arg Asp Ala Leu Leu Gly Asn Pro Gly Leu Ala Ser Arg Arg
            820                 825                 830

Val Arg Leu Glu Gln Val Ala Cys Arg Glu Pro Gly Trp Val Glu Leu
        835                 840                 845

His Val His Asp Asn Gly Gly Ile Glu Pro Leu Leu Leu Glu Arg
850                 855                 860

Ile Phe Glu Pro Phe Phe Thr Thr Lys Ala Glu Gly Lys Gly Thr Gly
865                 870                 875                 880

Leu Gly Leu Ser Val Ser His Asp Leu Val Arg Asn Met Gly Gly Ser
                885                 890                 895

Leu Thr Ala Ala Asn Gln Gly Glu Gly Ala Leu Phe Val Val Arg Leu
            900                 905                 910

Pro Leu Ala Ala Pro Ala Glu Ala Gly Gly
        915                 920

<210> SEQ ID NO 4
<211> LENGTH: 275
<212> TYPE: PRT
<213> ORGANISM: Pseudomonas aeruginosa

<400> SEQUENCE: 4

Met Asp Lys Pro Ala Ser Arg His Phe Ser Val Leu Ile Ile Asp Asp
1               5                   10                  15

Glu Pro Gln Val Thr Ser Glu Leu Arg Glu Leu Leu Glu Asn Ser Gly
            20                  25                  30

Tyr Arg Cys Val Thr Ser Thr His Arg Glu Ser Ala Ile Ala Ser Phe
        35                  40                  45

Gln Ala Asp Pro Asn Ile Gly Leu Val Ile Cys Asp Leu Tyr Leu Gly
    50                  55                  60

Gln Asp Asn Gly Ile Arg Leu Ile Glu Ser Leu Lys Glu Val Ala Gly
65              70                  75                  80

Asn Gly Arg Phe Phe Glu Ser Ile Ile Leu Thr Gly His Asp Gly Arg
                85                  90                  95

Gln Glu Val Ile Glu Ala Met Arg Val Gly Ala Ala Asp Tyr Tyr Gln
            100                 105                 110

Lys Pro Val Ala Pro Gln Glu Leu Leu His Gly Leu Glu Arg Leu Glu
        115                 120                 125

Ser Arg Leu His Glu Arg Val Arg Ser Gln Leu Ser Leu Ser His Val
    130                 135                 140

Asn Gln Arg Leu Glu Tyr Leu Ala Glu Ser Leu Asn Ser Ile Tyr Arg
145                 150                 155                 160

Asp Ile His Lys Ile Lys Tyr Glu Val His Gly Asn Ser Gln Pro Ser
                165                 170                 175

Ala Leu Arg Ser Glu Asp Ser Gln Pro Ser Ala Pro Ala Pro Val
            180                 185                 190

Ala Glu Ser Gln Val Ser Pro Ser Asn Pro Leu Phe Gly Lys Leu Ser
        195                 200                 205

Pro Arg Gln Gln Ala Val Ala Arg Leu Val Ser Lys Gly Leu Thr Asn
```

-continued

```
              210                 215                 220
Tyr Gln Ile Ala Tyr Glu Leu Gly Ile Thr Glu Asn Thr Val Lys Leu
225                 230                 235                 240

Tyr Val Ser Gln Val Leu Arg Leu Met His Met His Asn Arg Thr Gln
                245                 250                 255

Leu Ala Leu Ala Leu Ser Pro Ala Ala Met Gln Gln Gly Ser Gly Ala
                260                 265                 270

Val Val His
        275
```